United States Patent [19]

Szabó et al.

[11] Patent Number: 5,217,707
[45] Date of Patent: Jun. 8, 1993

[54] PHARMACEUTICAL COMPOSITION AND PROCESS FOR THE PREPARATION THEREOF

[75] Inventors: Anna Z. Szabó; Joszef Gaál; Katalin Mármarosi; Gyula Sebestyén; Gizella Miholics; Márta Kovcás, all of Budapest, Hungary

[73] Assignee: Chinoin Gyogyszer es Vegyeszeti Termekek Gara RT, Budapest, Hungary

[21] Appl. No.: 837,543

[22] Filed: Feb. 14, 1992

Related U.S. Application Data

[63] Continuation of Ser. No. 367,533, Jun. 16, 1989, abandoned.

[30] Foreign Application Priority Data

Jun. 16, 1988 [HU] Hungary ........................... 3088/88

[51] Int. Cl.5 .............................................. A61L 9/04
[52] U.S. Cl. .................................. 424/45; 424/401; 424/404; 424/405; 514/31; 514/36; 514/37
[58] Field of Search .................. 424/45, 6.5; 514/947; 534/31, 36, 37

[56] References Cited

U.S. PATENT DOCUMENTS

| | | | |
|---|---|---|---|
| 3,949,077 | 4/1976 | Buzna et al. | 424/114 |
| 4,404,189 | 9/1983 | Kulcsar et al. | 424/114 |
| 4,557,934 | 12/1985 | Cooper | 424/949 |
| 4,734,432 | 3/1988 | Szego et al. | 514/469 |
| 4,782,141 | 11/1988 | Dekany et al. | 536/122 |
| 4,963,367 | 10/1990 | Ecanow | 424/485 |
| 5,064,815 | 11/1991 | Szentmiklosi et al. | 514/31 |

FOREIGN PATENT DOCUMENTS

1512604  6/1978  United Kingdom .

OTHER PUBLICATIONS

Merck Index, 10th Ed., Compound 7652.
Merck Index, 11th Ed., Compound 7756.

*Primary Examiner*—Thurman K. Page
*Assistant Examiner*—Leon R. Horne
*Attorney, Agent, or Firm*—Herbert Dubno; Jonathan Myers

[57] ABSTRACT

The invention relates to a stabile, aqueous suspoemulsion containing as active ingredient 0.2-5 weight % of primycin, 5-25 weight % of propylene glycol, 0.5-5 weight % of non-ionic surface active agent, if desired 15 weight % of auxiliary agent and distilled water in an amount necessary to 100 weight %, as well as to a process for the preparation thereof.

9 Claims, No Drawings

PHARMACEUTICAL COMPOSITION AND PROCESS FOR THE PREPARATION THEREOF

This is a continuation of co-pending application Ser. No. 07/367,533 filed on Jun. 16, 1989, which is now abandoned.

FIELD OF THE INVENTION

The invention relates to a stabile aqueous suspoemulsion containing primycin as active ingredient and to a process for the preparation thereof. The invention relates furthermore to pharmaceutical compositions prepared from the stabile aqueous suspoemulsion.

BACKGROUND OF THE INVENTION

It is known that primycin (chemical name: 18-arabinozyl-2-n-butyl-3,7,11,15,19,21,23,25,27,37-decahydroxy-4,16,32,34,36-pentamethyl-tetrakonta-16,32-dien-35-0-lacton-40-quanidiniumsulfate) can successfully be used for treating skin diseases, urological diseases in surgery, ophthalmology, gynecology, and dermatology, as well as in the treatment of burns.

Neither resistant nor allergic reactions were found until now during its use. Furthermore combinations of primycine with other antibiotics are also known (HU-PS 158,241).

Primycin is used in different forms. HU-PS 173,708 describes pharmaceutical compositions containing heterocolloidal primycin. Disadvantages of these compositions are their low primycin content (0.2–1%), the ethanol used for preparing the heterocolloidal solvent has in certain cases a skin irritating effect as well as if the alcohol evaporates from the treated surface, a part of the primycin brought up to the surface runs off without biological utilization. HU-PS 194,493 described a basic gel containing primycin and N-methyl-pyrrolidone and the pharmaceutical compositions which can be prepared therefrom, such as a gel or, ointment.

OBJECT OF THE INVENTION

The object of the invention is to prepare a stabile aqueous basic composition having a high active ingredient content, which is alcohol-free, its organic solvent and surface active material content is low, and in addition it is suitable for preparing many different forms of medicines.

SUMMARY OF THE INVENTION

The invention is an aqueous suspoemulsion containing primycin as active ingredient, which contains 0.2–5 weight % of primycin, 5–25 weight % of propylenglycol, 0.5–5 weight % of non-ionic surface active agent and, if desired 15 weight % of other auxiliary agent, and distilled water in an amount necessary to reach 100 weight %.

The stabile aqueous suspoemulsion according to the invention can be prepared by dissolving or suspending warmly 0.2–5 weight % of primycin related to the end product in 5–25 weight % of propylenglycol and mixing the obtained solvent or suspension coldly or warmly with 0.5–5 weight % of non-ionic surface active agent, 0–15 weight % of other auxiliary agent, then with water in an amount necessary to 100 weight %.

The stabile aqueous suspoemulsion according to the invention can also be used in itself or by using known methods of pharmaceutical production and can be transformed into compositions usable as pharmaceuticals and as pharmaceutical cosmetics, such as a gel, ointment, foam aerosol, bandage, or plaster.

In addition to primycin the compositions according to the invention can contain other known antimicrobial active ingredient, as sisomycin, nethylmycin, doxycycline, gentamycin, norfloxacin, perfloxacin, cyprofloxacin, o-floxacin too.

A non-ionic surface active agent, the ether of polyethyleneglycol formed with lauryl, cetyl, stearyl or oleylalcohol, a sorbitan fatty acid ester or preferably an ethoxylated stearyl-alcohol can be used.

By using primycin having a particle size under 10 μm the active ingredient content of the compositions according to the invention can be increased. The stabile aqueous suspoemulsion can especially preferably be used for preparing foam aerosols suitable for treating burnt surfaces.

The characteristics of the foam compositions-a/loose, collapses soon; b/loose but stady; b/hard-can be influenced by varying the concentration of the suitably choosen non-ionic surface active agent, preferably ethoxylated stearyl-alcohol (Polawax A 31).

| The amount of Polawax A 31 | Foam density | Precipitation | time |
|---|---|---|---|
| 1 weight % | 0.26 g./cm$^3$ | <60 minutes | >3 hours |
| 1.5 weight % | 0.24 g./cm$^3$ | <60 minutes | >7 hours |
| 2.0 weight % | 0.22 g./cm$^3$ | <60 minutes | >12 hours |
| 2.5 weight % | 0.2 g./cm$^3$ | | >24 hours |

The hard foam prepared from the stabile aqueous suspoemulsion according to the invention steadily adheses on the surface, covers the wound for a long time, ensures a bacterium-free environment and sometimes makes the use of bandage superfluous.

In the foam aerosol compositions such as Freon, propane-butane, isobutane or dinitrogenoxide are used as propellants.

The stability of the aqueous suspoemulsion of the invention was examined by microbiological evaluation and by an organoleptic method.

The standard (Chinoin-Ebrimycin 841201=1066 mcg./mg.) and the test material of Example 2 were dissolved into a measuring flask by 500 ml. of a mixture of butanol:ethanol:water in a ratio 1:1:2. The concentration of the thus-obtained strain solutions was 4 mcg./ml. from which the following diluting lines were prepared:

| Standard 4 mcg./ml. | Amount measured from the solution of test material according to the invention 4 mcg./ml |
|---|---|
| 0.80 ml | |
| 0.75 ml | 0.75 ml |
| 0.70 ml | 0.70 ml |
| 0.65 ml | 0.65 ml |
| 0.60 ml | 0.60 ml |
| 0.55 ml | 0.55 ml |

The test organism used was: Streptococcus ATCC 8043. Culture medium: Standard Difco bouillon. The amount of inoculum was defined in a manner that the transmission should have been 95% of that compared to the (blind) culture medium without bacterium. 10 ml. of culture medium inoculated as described above were measured to each pre-prepared test tube.

Incubating temperature: 37° C., incubation time: 3-5 hours. Number of parallel measurements: 3

The measuring was carried out on spectrophotometer (Spektronom 195) at a wave-length of 570 nm by using a cuvet of 4 cm. The results were evaluated on the basis of the rules of mathematical statistics. On the basis of the microbiological comparative examinations it was found that the primycin content of the aqueous suspoemulsion according to the invention changed within a range of 5%.

By examining the aqueous suspension according to the invention orgenoleptic means it can be stated that by storing at 37° C. the suspoemulsion does not suffer organoleptic change for 1 year.

From the aqueous suspoemulsion according to the invention the utilization of the active ingredient was tested by defining the MIC-value (minimal inhibiting concentration). As comparative material the current primycin containing Ebrymycin gel (HU-PS 173,708) was used.

Taking the actual primycin active ingredient content of the Ebrymycin gel determined by previous microbiological value determination and the aqueous primycin suspoemulsion of 1 weight % into consideration concentration series were prepared. The MIC determinations were carried out in accordance with the classic microbiological rules.

Used culture medium: Standard Difco bouillon
Incubating temperature: 37° C.
Incubation time: 24 hours
Used test organisms:
Staphylococcus aureus HNCMB 112002
Staphylococcus aureus HNCMB 112003
Staphylococcus aureus HNCMB 110002
Streptococcus faecalis HNCMB 80171
Streptococcus pyogeues HNCMB 80001
Escherichia coli HNCNB 35033
Pseudomonas aeruqinosa HNCNB 170021
Number of parallel measurements: 3

The results of our examinations are summarized in Tables 1 to 6 as follows:

TABLE 1

| Concentration of sample in the test tube (μg./ml.) | Streptococcus faecalis HNCMB 80171 | | |
|---|---|---|---|
| | Ebrymycin gel MIC | Suspoemulsion according to | |
| | | Example 2 MIC | Example 12 MIC |
| 0.01 | + | + | + |
| 0.05 | + | + | + |
| 0.1 | + | + | − |
| 0.5 | + | − | − |
| 0.75 | + | − | − |
| 1,0 | + | − | − |
| 1.5 | + | − | − |
| 2.0 | + | − | − |
| 3.0 | + | − | − |
| 5.0 | − | − | − |
| 10.0 | − | − | − |

TABLE 2

| Concentration of sample in the test tube (μg./ml.) | Streptococcus pyogenis HNCMB 80001 | | |
|---|---|---|---|
| | Ebrymycin gel MIC | Suspoemulsion according to | |
| | | Example 2 MIC | Example 12 MIC |
| 0.01 | + | + | + |
| 0.05 | + | + | + |
| 0.1 | + | − | − |
| 0.5 | + | − | − |
| 0.75 | + | − | − |
| 1,0 | − | − | − |
| 1.5 | − | − | − |
| 2.0 | − | − | − |
| 3.0 | − | − | − |
| 5.0 | − | − | − |

TABLE 3

| Concentration of sample in the test tube (μg./ml.) | Staphylococcus aureus HNCMB 110002 | | |
|---|---|---|---|
| | Ebrymycin gel MIC | Suspoemulsion according to | |
| | | Example 2 MIC | Example 12 MIC |
| 0.01 | + | + | + |
| 0.05 | + | + | − |
| 0.1 | + | − | − |
| 0.5 | + | − | − |
| 0.75 | + | − | − |
| 1,0 | + | − | − |
| 1.5 | − | − | − |
| 2.0 | − | − | − |
| 3.0 | − | − | − |
| 5.0 | − | − | − |

TABLE 4

| Concentration of sample in the test tube (μg./ml.) | Staphylococcus aureus HNCMB 112003 | | |
|---|---|---|---|
| | Ebrymycin gel MIC | Suspoemulsion according to | |
| | | Example 2 MIC | Example 12 MIC |
| 0.01 | + | + | + |
| 0.05 | + | + | + |
| 0.1 | + | + | + |
| 0.5 | + | − | − |
| 0.75 | + | − | − |
| 1,0 | + | − | − |
| 1.5 | + | − | − |
| 2.0 | − | − | − |
| 3.0 | − | − | − |
| 5.0 | − | − | − |

TABLE 5

| Concentration of sample in the test tube (μg./ml.) | Staphylococcus aureus HNCMB 112002 | | |
|---|---|---|---|
| | Ebrymycin gel MIC | Suspoemulsion according to | |
| | | Example 2 MIC | Example 12 MIC |
| 0.01 | + | + | + |
| 0.05 | + | + | + |
| 0.1 | + | − | − |
| 0.5 | + | − | − |
| 0.75 | + | − | − |
| 1,0 | − | − | − |
| 2.0 | − | − | − |
| 3.0 | − | − | − |
| 5.0 | − | − | − |

TABLE 6

| Concentration of sample in the test tube (μg./ml.) | Escherichia coli HNCNB 35033 | Pseudomonas aeruqinosa HNCNB 170021 |
|---|---|---|
| | Suspoemulsion according to Example 12 MIC | |
| 0.01 | + | + |
| 0.05 | + | + |
| 0.1 | + | − |
| 0.5 | + | − |
| 0.75 | + | − |
| 1.0 | − | − |
| 2.0 | − | − |
| 3.0 | − | − |

TABLE 6-continued

| Concentration of sample in the test tube (µg./ml.) | Escherichia coli HNCNB 35033 | Pseudomonas aeruqinosa HNCNB 170021 |
|---|---|---|
| | Suspoemulsion according to Example 12 MIC | |
| 5.0 | — | — |

Evaluating the results it can be stated, that the aqueous suspoemulsion containing 1 weight % of primycin has about 10 times better biological utilization (on the pyogenic cocci above tested), than Ebrymycin gel.

By well controlled comparative tests conducted under industrial conditions it was determined, whether the composition is effective against clinical mastitis. The effectivity was compared with that of the current Mamylin (Germed, GDR) veterinary composition of similar effectivity containing an ingredient with the same activity.

In a dairy farm the test comprised all the newly diagnosed cases showing the clinical symptoms of one type of the acute mastitis.

After samples were taken the medical treatment was carried out as follows: after the concerned udder quarters had been carefully milked out the test composition was administered intramammally (intracysternally). The content of a plastic syringe was injected in each case. The treatment was repeated similarly day after day for several days if the clinical status of the udder quarter so required. Before the medical treatment or by the control test the cultured bacteria were determined from the milk samples gathered under aseptic conditions, while determining their total germ number, and the antibiotic sensitivity examinations thereof was carried out.

When initiating the animals in the test, before beginning the medical treatment, the acute udder changes were put on the basis of the type of the clinical symptoms among two main groups (catarrhal, parenchymal mastitis), within which several subgroups were distinguished on the basis of the seriousness of the symptoms. The classification was carried out on the basis of the points of view given by CSEH (1973), HORVÁTH (1983) and PYÖRALA (1988) adapted to the test conditions.

The change of the test conditions obtained as a result of the medical treatment was examined daily. The final estimation was made daily on the basis of the control test carried out on the 10–22nd day after the last treatment (clinical, Mastitest, microbiological test).

Considering the points of view given by HORVÁTH (1982, 1983) also the udder quarter was considered to be recovered if no clinical symptoms or milk changes in quantity or quality, relating to the inflammation were found, and furthermore if the results of the Mastitest examination of the secretion of glands and the microbiological test were negative. The case was considered as improved when the recovery had taken place with a little interstitial induration residue and by the permanent decrease of lower degree of the milk secretion. When in the control test, Mastitest positivity was found it was described in terms of the decrease of the progress of the disease into subclinical states, while in the case where the microbiological control test result was positive, about the remission of infection of the udder quarter. In some cases the complete and definite drying up could be observed.

The tests comprised 42 freshly sickened udder quarters of 35 animals. From this 32 udder quarter-change of 38 cows is catarrhal and 10 udder quarters of 7 animals proved to be parenchymal mastitis.

The classification of the test animals into groups are contained in Table 7.

About ⅔ of the test animals was subjected to bacteriological test. When examining the catarrhal udder quarters having mastitis also by microbiological methods before medical treatment, it was found that more than ⅓ proved to be bacteriologically negative.

In cases of galactephoromastitis of different degrees each isolated bacteria was pathogenic showing positive tinction (Str. or Staph.) according to Gram.

Each of the 32 udder quarters of the 28 animals sickened in galactophoromastitis of different degrees recovered (69%) or at least became symptom-free (31%). Generally 2 or 3 treatments were enough for the complete recovery (Table 8).

According to expectations in case of acute mastitis parenchymatosa the effectivity of the medical treatment was unfavorable: from the 10 sickened udder quarters of 7 animals only 6 quarters recovered, 3 improved or lessened into remission or subclinical case, while 1 milked out.

From the comparison (Table 8) it can be stated that the test treatment resulted in a recovery of a larger extent both in the case of catarrhal and the paranchymal mastitis, by using the composition of Example 12 instead of MAMYCINE.

TABLE 7

| | Number of the treated and control groups | | | |
|---|---|---|---|---|
| | Catarrhal mastitis | | Paranchymal mastitis | |
| | cow | udder quarter | cow | udder quarter |
| Composition according to Example 12 | 28 | 20 | 4 | 6 |
| Mamycin | 10 | 12 | 3 | 4 |
| Total | 38 | 32 | 7 | 10 |

TABLE 8

| | Catarrhal udder quarters | | | Paranchymal mastitis udder quarter | | |
|---|---|---|---|---|---|---|
| | treated | recovered | improved | treated | recovered | improved |
| Composition according to Example 12 | 20 100% | 17 85% | 3 15% | 6 100% | 4 67% | 2 33% |
| Mamycin | 12 100% 32 | 7 58% 22 | 5 42% 10 | 4* 100% 10 | 2 50% 6 | 1 25% 3 |

* = one udder quarter milked out
Mamycin: (produced by Germed) active ingredient: benzyl-penicillin-K and streptomycin-sulphate The compositions according to the invention are illustrated in the following non-limiting Examples.

EXAMPLE 1

Aqueous suspoemulsion with the following composition is prepared:

| Primycin | 0.2 weight % |
|---|---|
| Propylenglycol | 15 weight % |
| Polawax A 31 | 0.5 weight % |
| Distilled water ad | 100 weight % |

The pH of the composition is adjusted by Na$_2$HPO$_2$2H$_2$O to pH=8.

EXAMPLE 2

Aqueous suspoemulsion with the following composition is prepared:

| | |
|---|---|
| Primycin | 1 weight % |
| Propylenglycol | 15 weight % |
| Polawax A 31 | 2.0 weight % |
| Distilled water ad | 100 weight %. |

The pH of the composition is adjusted with Na$_2$HPO$_4$2H$_2$O to pH=8.

EXAMPLE 3

Aqueous suspoemulsion with the following composition is prepared:

| | |
|---|---|
| Primycin | 1.5 weight % |
| Propylenglycol | 25 weight % |
| Polawax A 31 | 2.5 weight % |
| Distilled water ad | 100 weight %. |

The pH of the composition is adjusted with Na$_2$HPO$_4$2H$_2$O to pH=8.

EXAMPLE 4

Aqueous suspoemulsion with the following composition is prepared:

| | |
|---|---|
| Microcrystalline primycin | 5 weight % |
| Propylenglycol | 15 weight % |
| Polawax A 31 | 3 weight % |
| Distilled water ad | 100 weight %. |

The pH of the composition is adjusted with Na$_2$HPO$_4$2H$_2$O to a value of 8.

EXAMPLE 5

The foam aerosol of the following composition is prepared:

| | |
|---|---|
| Composition of Example 4 | 85–90 weight % |
| Propellant (Freon 12/114, 50:50) | 10–15 weight %. |

EXAMPLE 6

A gel with the following composition is prepared:

| | |
|---|---|
| Suspoemulsion according to Example 4 | 50 weight % |
| Carbopol 934 | 2 weight % |
| Triethanolamine | 0.5 weight % |
| Conserving agent (Nipagin-M) | 0.1–0.2 weight % |
| Distilled water ad | 100 weight %. |

EXAMPLE 7

An ointment of the following composition is prepared:

| | |
|---|---|
| Suspoemulsion of Example 4 | 85 weight % |
| Cetyl-stearyl-alcohol | 10 weight % |
| Glycerine | 4.8–4.9 weight % |
| Preservative (Nipagin-M) | 0.1–0.12 weight %. |

EXAMPLE 8

A gauze sheet of the following composition is prepared:

| | |
|---|---|
| Suspoemulsion of Example 4 | 97.5 weight % |
| Polyvinyl-pyrrolidone | 0.5 weight % |
| Distilled water ad | 100 weight %. |

The composition is applied to a gauze sheet under sterile conditions and closed.

EXAMPLE 9

The composition of Example 8 is applied to a sterile gauze sheet and as cover sheet thin, impregnated, shadow-proof linen of adhesive surface is used.

EXAMPLE 10

An aqueous suspension of the following composition is prepared:

| | |
|---|---|
| Primycin | 3 weight % |
| Gentamycin | 0.2 weight % |
| Propylenglycol | 20 weight % |
| Polawax A 31 | 3.5 weight % |
| Distilled water ad | 100 weight %. |

The pH of the composition is adjusted with Na$_2$HPO$_4$2H$_2$O to a value of 8.

EXAMPLE 11

A foam aerosol with the following composition is prepared:

| | |
|---|---|
| Composition of Example 4 | 80–85 weight % |
| Propellant (Propane-butane) | 15–20 weight %. |

EXAMPLE 12

Aqueous composition of the following composition is prepared:

| | |
|---|---|
| Primycin | 4 weight % |
| Streptomycin-sulphate | 2.6 weight % |
| Propylenglycol | 16.0 weight % |
| Polawax A 31 | 3.5 weight % |
| Prednisolone | 1.0 weight % |
| Distilled water ad | 100 weight %. |

We claim:

1. A stable, aqueous, suspoemulsion which consists essentially of:
   0.2 to 5% by weight primycin;
   5 to 25% by weight propylene glycol;
   0.5 to 5% by weight of a nonionic surface active agent; and;
   balance distilled water.
2. The suspoemulsion as defined in claim 1 wherein the nonionic surface active agent is an ether of polyethylene glycol formed with lauryl, cetyl, stearyl, or oleyl alcohol; a sorbitan fatty acid ester; or an ethoxylated stearyl alcohol.

3. The suspoemulsion as defined in claim 1 wherein the primycin has a particle size under 10 microns.

4. An antibacterial composition consisting essentially of as active ingredient the primycin-containing stable, aqueous suspoemulsion of claim 1 in an amount of 50 to 100% by weight and a filling, diluting or other pharmaceutical inert auxiliary agent in an amount up to 20% by weight.

5. An antibacterial composition in the form of a stable foam with regulated transmission of the active ingredient for treating a wound surface, which consists essentially of:
   0.2 to 4.5% by weight primycin;
   12.5 to 23% by weight propylene glycol;
   0.8 to 2.3% by weight of a nonionic surface active agent;
   0 to 2% by weight of a second antimicrobial agent;
   10 to 20% of a foam-forming agent; and
   balance distilled water.

6. A process for preparing a stable, aqueous suspoemulsion as defined in claim 1 containing as active ingredient, primycin, which comprises the steps of dissolving or suspending warmly 0.2 to 5% by weight of primycin, relative to the end product, in 5 to 25% by weight of propylene glycol, then mixing the obtained solution or suspension with 0.5 to 5% by weight of a nonionic surface active agent, and then with water which comprises the balance of the composition.

7. A process for preparing an antibacterial composition defined in claim 4 which comprises transforming the aqueous stable, suspoemulsion containing primycin as active ingredient into a pharmaceutical or a pharmaceutical-cosmetic composition by using filling or diluting inert auxiliary agents, and optionally adding a second antimicrobial active agent.

8. A process for preparing an antimicrobial composition as defined in claim 7 which comprises formulating the composition in the form of a gel, ointment, foam, aerosol, or as a bandage.

9. An antibacterial composition consisting essentially of as active ingredients, the primycin-containing stable, aqueous suspoemulsion of claim 1 in an amount of 50 to 99.8% by weight and a compound selected from the group consisting of sisomicin, methylmycin, doxycycline, gentamycin, norfloxacin, perfloxacin, cyprofloxacin, O-floxacin, and streptomycin, in an amount of 0.2 to 5% by weight, and a pharmaceutically acceptable inert carrier in an amount up to 20% by weight.

* * * * *